US00PP28698P3

(12) United States Plant Patent
Wood

(10) Patent No.: US PP28,698 P3
(45) Date of Patent: Nov. 28, 2017

(54) ***HYDRANGEA* PLANT NAMED 'SMHMEPSILON'**

(50) Latin Name: ***Hydrangea* hybrid**
Varietal Denomination: SMHMEPSILON

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 24 days.

(21) Appl. No.: 14/998,624

(22) Filed: Jan. 20, 2016

(65) Prior Publication Data

US 2017/0208720 P1 Jul. 20, 2017

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct *Hydrangea* cultivar named 'SMHMEPSILON' is disclosed, characterized by lace-cap inflorescence, early flowering and strong, continuous blooming. The new variety is a *Hydrangea,* normally produced as an ornamental plant for containers or gardens.

2 Drawing Sheets

Latin name of the genus and species: *Hydrangea* hybrid. Variety denomination: 'SMHMEPSILON'.

BACKGROUND OF THE INVENTION

The new *Hydrangea* cultivar is a product of a planned breeding program conducted by the inventor, Timothy D. Wood, in Grand Haven, Mich. The objective of the breeding program was to produce new *Hydrangea* varieties. The open pollination resulting in this new variety was made during July of 2008.

The seed parent is the patented commercial variety *Hydrangea macrophylla* 'Robert' U.S. Plant Pat. No. 20,020. The pollen parent is unknown, as it was an open pollination breeding program. The new variety was identified as a potentially interesting selection in June of 2011, at a greenhouse in Grand Haven, Mich.

Asexual reproduction of the new cultivar 'SMHMEPSILON' by softwood cuttings was first performed during the June of 2011, at commercial greenhouse in Grand Haven, Mich. Subsequent propagation has shown that the unique features of this cultivar are stable and reproduced true to type in 4 successive generations.

SUMMARY OF THE INVENTION

The cultivar 'SMHMEPSILON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMHMEPSILON' These characteristics in combination distinguish 'SMHMEPSILON' as a new and distinct *Hydrangea* cultivar:

1. Lace-cap inflorescence.
2. Early flowering.
3. Strong continuous bloomer.

PARENT COMPARISON

Plants of the new cultivar 'SMHMEPSILON' are similar to plants of the seed parent, *Hydrangea macrophylla* 'Robert' in most horticultural characteristics, however, plants of the new cultivar 'SMHMEPSILON' differ in the following:

1. Lacecap inflorescence. Seed parent has a mophead inflorescence.
2. Earlier flowering
3. Stronger flowering stems.

Pollen parent unknown as this is product of open pollination.

COMMERCIAL COMPARISON

'SMHMEPSILON' can be compared to the patented commercial variety *Hydrangea* 'MAK20' U.S. Plant Pat. No. 24,820. These varieties are similar in most horticultural characteristics; however 'SMHMEPSILON' differs in the following:

1. Taller plant.
2. Larger inflorescence width.

BRIEF DESCRIPTION OF THE PHOTOGRAPHS

Figure 1:
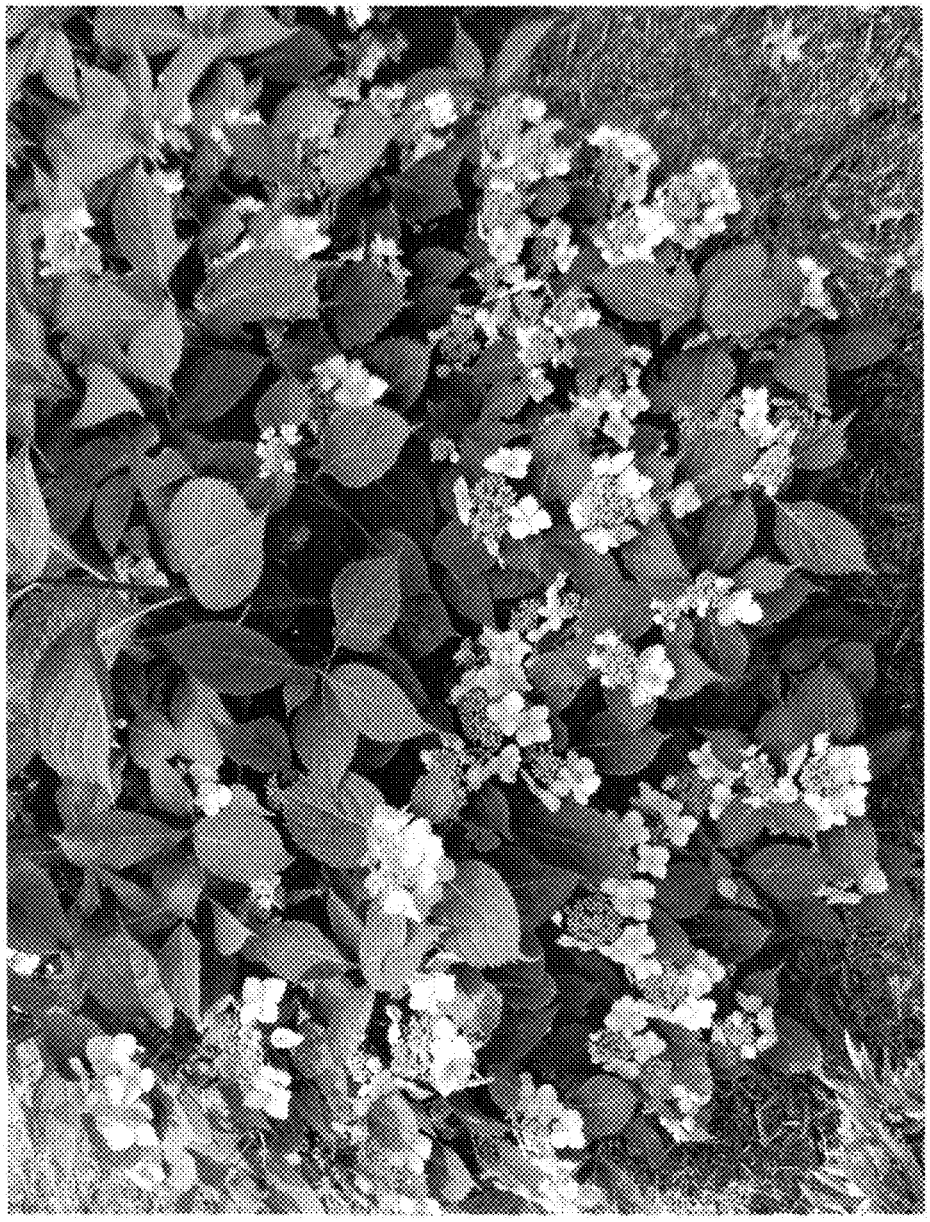

The accompanying photograph in FIG. 1 illustrates in full color a typical flowering plant of 'SMHMEPSILON' grown outdoors in Grand Haven, Mich., USA, in a field.

Figure 2:
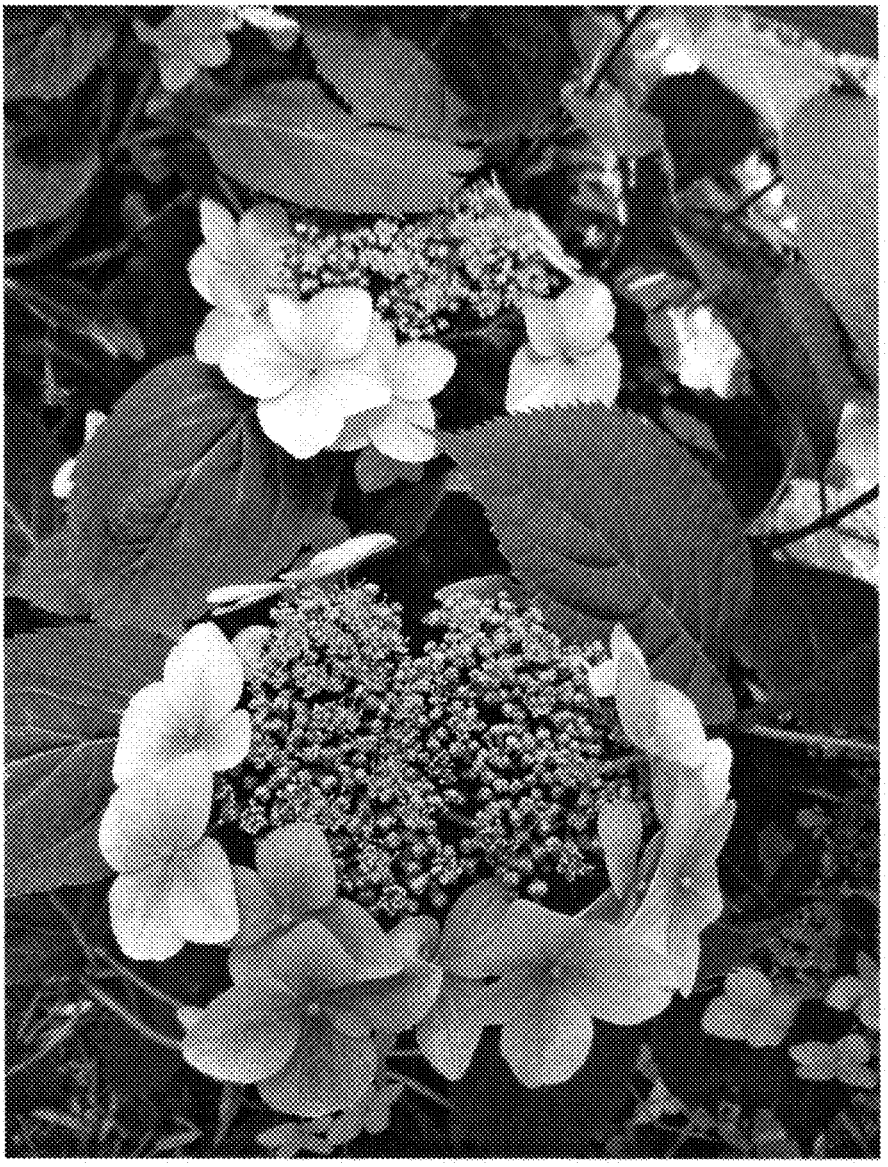

FIG. 2 illustrates in full color a close up view of the inflorescence. Inflorescences on the plant in FIG. 1 are less mature than those in FIG. 2. Age of the plant photographed is approximately 2-3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 1996 Royal Horticultural Society Colour Chart except where general terms of ordinary dictionary significance are used. The following observations and measurements describe 'SMHMEPSILON' plants grown in a double layered poly greenhouse, in Grand Haven, Mich., USA. The growing temperature ranged from approximately 18° C. to 27° C. daytime and 5° to 10° C. at night. Measurements and numerical values represent averages of typical plant types. Measurements were taken during July of 2015.

Botanical classification: *Hydrangea* hybrid 'SMHMEPSILON'.

PROPAGATION

Time to initiate roots: Approximately 18 days at approximately 27° C.

Time to produce a rooted young plants: Approximately 60 days at approximately 27° C.

Root description: Thick and fine, freely root branching and dense, fibrous. Color is white and brown.

Propagation method: Softwood cuttings.

PLANT

Age of plant described: 2-3 years.

Pot size: #2.

Growth habit: Flowering perennial shrub, round.

Overall plant shape: Round.

Height: 57 cm.

Plant spread: 42 cm.

Growth rate: Good.

Plant vigor: Good.

Branching characteristics: Opposite, basal branches, some pinching required.

Length of lateral branches: Approximately 45 cm.

Number of lateral branches: 15.

Diameter of lateral branches: 4 mm.

Lateral branch shape and appearance: Round.

Lateral branch strength: Good.

Internode length: 5 cm.

Branch color:

- *Immature*.—Near RHS Yellow-Green 145B.
- *Mature*.—Near RHS Yellow-Green 145B.

Branch aspect: 45°.

Branch pubescence: No.

FOLIAGE

Leaf:

- *Arrangement*.—Opposite.
- *Average length*.—12 cm.
- *Average width*.—10 cm.
- *Shape of blade*.—Ovate.
- *Apex*.—Acuminate.
- *Base*.—Rounded to obtuse.
- *Margin*.—Serrate.
- *Texture and appearance of top surface*.—Leathery, glossy
- *Texture and appearance of bottom surface*.—Glossy, coarse.
- *Color*.—Young foliage upper side: Near RHS Yellow-green 144A. Young foliage under side: Near RHS Yellow-green 146B. Mature foliage upper side: Near RHS Green 139A. Mature foliage under side: Near RHS Green 138B.
- *Venation*.—Type: Pinnate. Venation color upper side: Near RHS Yellow-green 145B. Venation color under side: Near Yellow-green 145B.

Petiole:

- *Average length*.—2.8 cm.
- *Diameter*.—3 mm.
- *Color*.—Upper side: Near RHS Yellow-green 145B. Under side: Near RHS Yellow-green 145B.
- *Texture upper side*.—Glossy, slight pubescence.
- *Texture under side*.—Glossy, slight pubescence.

FLOWER

Bloom period:

- *Natural season*.—Early Summer until Fall.

Inflorescence:

- *Type*.—Lacecap.
- *Quantity of flowers per inflorescence*.—Fertile flowers, 90 approximately. Sterile Flowers, 14 approximately.
- *Persistent or self-cleaning*.—Self-cleaning.
- *Fragrance*.—Lightly scented.

Panicle:

- *Shape*.—Round with a flattened top.
- *Height*.—4 cm.
- *Diameter*.—15 cm.

Sterile flower:

- *Androecium*.—Yes.
- *Bud shape*.—Obovate.
- *Bud length*.—4 mm.
- *Bud diameter*.—2.5 mm.
- *Bud color*.—Acidic: Near RHS Violet-blue 98B. Basic: Near RHS Purple 76B.
- *Flower aspect*.—Upright and outward.
- *Flower shape*.—Cruciform.
- *Flower length*.—3.8 cm.
- *Flower diameter*.—4 mm.
- *Flower depth*.—2 mm.

Sterile flower petals:

- *Petal arrangement*.—Whorl.
- *Length of petal*.—Approximately 2 mm.
- *Width of petal*.—Approximately 1 mm.
- *Apex*.—Acute.
- *Shape of petal*.—Ovate.
- *Petal margin*.—Entire.
- *Petal base*.—Obtuse/fused.
- *Petal number*.—4.
- *Petal texture*.—Smooth, upper and under side.
- *Color*.—Upper surface at first opening: Acidic: Near RHS Violet-blue 98B. Basic: Near RHS Purple 76B. Upper surface at maturity: Acidic: Near RHS Violet-blue 98B. Basic: Near RHS Purple 76B. Under surface at first opening: Acidic: Near RHS Violet-blue 98B. Basic: Near RHS Purple 76B. Under surface at maturity: Acidic: Near RHS Violet-blue 98B. Basic: Near RHS Purple 76B.

Sterile flower sepal:

- *Arrangement*.—Whorl.
- *Number*.—4.
- *Shape*.—Obovate.
- *Tip*.—Obtuse.

*Base*.—Cuneate.
*Margin*.—Entire.
*Length*.—2 mm.
*Width*.—2 mm.
*Texture, upper*.—Smooth.
*Texture, lower*.—Smooth.
*Color*.—Upper surface at first opening: Acidic: Near RHS Purple-violet 82C and Violet-Blue 93C at the base. Basic: Near RHS Red-purple 68B. Upper surface at maturity: Acidic: Near RHS Purple-violet 82C and Violet-Blue 93C at the base. Basic: Near RHS Red-purple 68B. Under surface at first opening: Acidic: Near RHS Purple-violet 82D and Violet-Blue 93D at the base. Basic: Near RES Red-purple 73B. Under surface at maturity: Acidic: Near RHS Purple-violet 82D and Violet-Blue 93D at the base. Basic: Near RHS Red-purple 73B. Fading to Upper surface: Acidic: Near RHS Purple-violet 82C and Violet-Blue 93C at the base. Basic: Near RHS Red-purple 73D. Fading to Under surface: Acidic: Near RHS Purple-violet 82D and Violet-Blue 93D at the base. Basic: Near RHS Red-purple 73D.

Sterile flower pedicel:
*Length*.—14 mm.
*Diameter*.—1 mm.
*Angle*.—Upright and outward.
*Strength*.—Good.
*Texture*.—Smooth.
*Color*.—Acidic: Near RHS Violet-blue 94C. Basic: Near RHS Red-purple 69A.

Fertile flower:
*Bud shape*.—Round to obovate.
*Bud length*.—2 mm.
*Bud diameter*.—2.5 mm.
*Bud color*.—Near RHS White 155B with Red-purple 63C on the top.
*Flower aspect*.—Upright and outward.
*Flower shape*.—Star-like.
*Flower length*.—6 mm.
*Flower diameter*.—4.5 mm.
*Flower depth*.—5 mm.

Fertile flower petals:
*Length of petal*.—2 mm.
*Width of petal*.—1 mm.
*Apex*.—Acute.
*Shape of petal*.—Ovate.
*Petal margin*.—Entire.
*Petal arrangement*.—Whorl.
*Petal number*.—5.
*Petal base*.—Rounded/obtuse.
*Petals fused*.—No.
*Petal texture*.—Smooth, upper and under side.
*Color*.—Upper surface at first opening: Acidic: Near RHS Blue 100C. Basic: Near RHS Red-purple 68C. Upper surface at maturity: Acidic: Near RHS Blue 100C. Basic: Near RHS Red-purple 68C. Under surface at first opening: Acidic: Near RHS Blue 100C. Basic: Near RHS Red-purple 68C. Under surface at maturity: Acidic: Near RHS Blue 100C. Basic: Near RHS Red-purple 68C. Upper surface fading to: Acidic: Near RHS Blue 100C. Basic: Near RHS Red-purple 68C. Lower surface fading to: Acidic: Near RHS Blue 100C. Basic: Near RHS Red-purple 68C.

Fertile flower pedicel:
*Angle*.—15-90°.
*Strength*.—Good.
*Length*.—2.5 mm.
*Width*.—0.5 mm.
*Texture*.—Smooth.
*Color*.—Acidic: Near RHS Blue 104B. Basic: Near RHS Red-purple 68B.

Fertile flower sepal:
*Arrangement*.—Whorl.
*Number*.—5.
*Shape*.—Triangular.
*Tip*.—Acute.
*Base*.—Ovate.
*Margin*.—Entire.
*Length*.—1 mm.
*Width*.—1 mm.
*Texture, upper*.—Smooth.
*Texture, lower*.—Smooth.
*Color*.—Upper surface at first opening: Acidic: Near RHS Blue 100C. Basic: Near RHS Red-purple 62C. Upper surface at maturity: Acidic: Near RHS Blue 100C. Basic: Near RHS Red-purple 62C. Under surface at first opening: Acidic: Near RHS Blue 100C. Basic: Near RHS Red-purple 62C. Under surface at maturity: Acidic: Near RHS Blue 100C. Basic: Near RHS Red-purple 62C. Upper surface fading to: Acidic: Near RHS Blue 100C. Basic: Near RHS Red-purple 62C. Lower surface fading to: Acidic: Near RHS Blue 100C. Basic: Near RHS Red-purple 62C.

REPRODUCTIVE ORGANS

Sterile flower:
*Stamen number*.—8.
*Filament length*.—1 mm.
*Filament color*.—Acidic: Near RHS Blue 105C. Basic: Near RHS Purple-violet 82A.
*Anther shape*.—Round.
*Anther color*.—Acidic: Near RHS Blue 106A. Basic: Near RHS Red-purple 62B.
*Anther length*.—1 mm.
*Pollen amount*.—Some.
*Pollen color*.—Inconspicuous.
*Gynoecium*.—Yes.
*Pistil number*.—1, two-lobbed.
*Pistil length*.—1 mm.
*Stigma shape*.—Lobed.
*Style length*.—1 mm.
*Style color*.—Acidic: Near RHS Violet-blue 98A. Basic: Near RHS Red-purple 64B.
*Ovary color*.—Acidic: Near RHS Violet-blue 98A. Basic: Near RHS Red-purple 64B.

Fertile flower:
*Stamen number*.—5-10.
*Filament length*.—5 mm.
*Filament color*.—Acidic: Near RHS Blue 104A. Basic: Near RHS Red-purple 68B.
*Anther shape*.—Oblong.
*Anther length*.—1 mm.
*Anther color*.—Near RHS Greyed-green 197B.
*Pollen amount*.—Some.
*Pollen color*.—Near RHS White 155B.

*Pistil number.*—1, two-lobed and three-lobed.

*Pistil length.*—5 mm.

*Stigma shape*.—Lobed.

*Stigma color*.—Acidic: Near RHS Blue 104B. Basic: Near RHS Red-purple 73C.

*Style length.*—2 mm.

*Style color*.—Acidic: Near RHS Blue 104B. Basic: Near RHS Red-purple 63C.

*Ovary color*.—Acidic: Near RHS Blue 100D. Basic: Near RHS Red-purple 73D.

OTHER CHARACTERISTICS

Disease resistance: Neither resistance nor susceptibility to diseases or pests has been observed in this variety.

Cold tolerance: −31° C. to 38° C.

Fruit/seed production: 1000's of seeds produced. Abundant, minute seed produced. Seed less than 1 mm in diameter and length, brown, too small to accurately measure with R.H.S. chart.

What is claimed is:

1. A new and distinct cultivar of *Hydrangea* plant named 'SMHMEPSILON' as herein illustrated and described.

* * * * *